United States Patent
Hidalgo Vivas et al.

(10) Patent No.: US 10,150,714 B2
(45) Date of Patent: Dec. 11, 2018

(54) PROCESS AND CATALYST FOR UPGRADING GASOLINE

(71) Applicant: Haldor Topsøe A/S, Kgs. Lyngby (DK)

(72) Inventors: Angelica Hidalgo Vivas, Herlev (DK); Finn Joensen, Hørsholm (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 14/403,274

(22) PCT Filed: Mar. 20, 2013

(86) PCT No.: PCT/EP2013/055758
§ 371 (c)(1),
(2) Date: Nov. 24, 2014

(87) PCT Pub. No.: WO2013/178375
PCT Pub. Date: Dec. 5, 2013

(65) Prior Publication Data
US 2015/0094510 A1  Apr. 2, 2015

(30) Foreign Application Priority Data

May 29, 2012  (DK) ................................ 2012 70284

(51) Int. Cl.
| | |
|---|---|
| C10G 45/58 | (2006.01) |
| C07C 5/27 | (2006.01) |
| B01J 29/46 | (2006.01) |
| C10G 45/64 | (2006.01) |
| C10L 1/06 | (2006.01) |
| B01J 27/043 | (2006.01) |
| B01J 29/40 | (2006.01) |

(52) U.S. Cl.
CPC ........... *C07C 5/2775* (2013.01); *B01J 27/043* (2013.01); *B01J 29/40* (2013.01); *B01J 29/46* (2013.01); *C07C 5/2737* (2013.01); *C10G 45/64* (2013.01); *C10L 1/06* (2013.01); *B01J 2229/186* (2013.01); *C07C 2529/46* (2013.01)

(58) Field of Classification Search
None
See application file for complete search history.

(56) References Cited

U.S. PATENT DOCUMENTS

| | | | | |
|---|---|---|---|---|
| 3,269,937 A | * | 8/1966 | Maxwell | B01J 27/04 208/135 |
| 3,562,342 A | * | 2/1971 | Gayle | B01J 29/076 208/2 |

(Continued)

FOREIGN PATENT DOCUMENTS

FR  2 189 120 A1  1/1974

*Primary Examiner* — Philip Y Louie
(74) *Attorney, Agent, or Firm* — Blank Rome LLP

(57) ABSTRACT

Process and catalyst for upgrading gasoline comprising durene (1,2,4,5-tetramethylbenzene) and pseudodocumene, the process comprises hydroisomerization of durene (1,2,4,5-tetramethylbenzene) and pseudocumene (1,2,4-trimethylbenzene) contained in the gasoline in presence of a catalyst comprising a sulfided base metal supported on an acidic carrier, thereby converting durene (1,2,4,5-tetramethylbenzene) to isodurene (1,2,4,5-tetramethylbenzene) and prehnitene (1,2,3,4-tetramethylbenzene) and converting pseudocumene (1,2,4-trimethylbenzene) to mesitylene (1,3,5-trimethylbenzene).

11 Claims, 2 Drawing Sheets

Formation of C3-C7 hydrocarbons as a function of sulphur content

(56) References Cited

U.S. PATENT DOCUMENTS

| | | | | |
|---|---|---|---|---|
| 3,619,408 | A | * | 11/1971 | Larson ............... C10L 1/06 208/138 |
| 3,776,968 | A | | 12/1973 | Bushick et al. |
| 3,912,659 | A | * | 10/1975 | Brandenburg ......... B01J 29/20 502/66 |
| 4,127,471 | A | | 11/1978 | Suggitt et al. |
| 4,304,951 | A | * | 12/1981 | Garwood ............ C10G 45/44 585/469 |
| 4,384,471 | A | * | 5/1983 | Wentzel ............. G01N 30/08 422/89 |
| 4,387,261 | A | * | 6/1983 | Chester .............. C07C 4/18 208/66 |
| 4,508,836 | A | * | 4/1985 | Haag ................. B01J 29/40 502/53 |
| 5,004,854 | A | | 4/1991 | Yan |
| 5,576,256 | A | * | 11/1996 | Monque .............. B01J 29/061 502/61 |
| 2010/0041932 | A1 | * | 2/2010 | Dodwell ............. B01J 29/06 585/469 |
| 2011/0166396 | A1 | | 7/2011 | Egeberg et al. |
| 2012/0116137 | A1 | * | 5/2012 | Fang ................. B01J 8/0449 585/317 |

* cited by examiner

Figure 1. Formation of C3-C7 hydrocarbons as a function of sulphur content
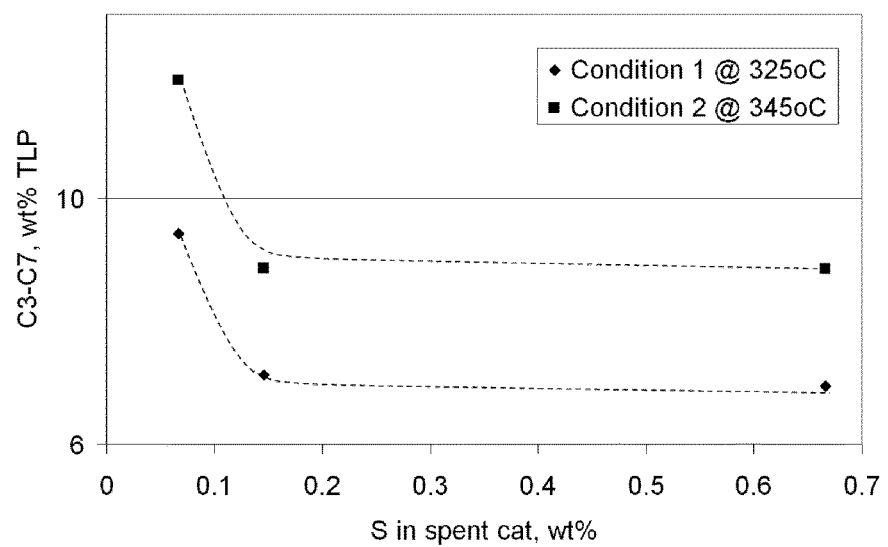

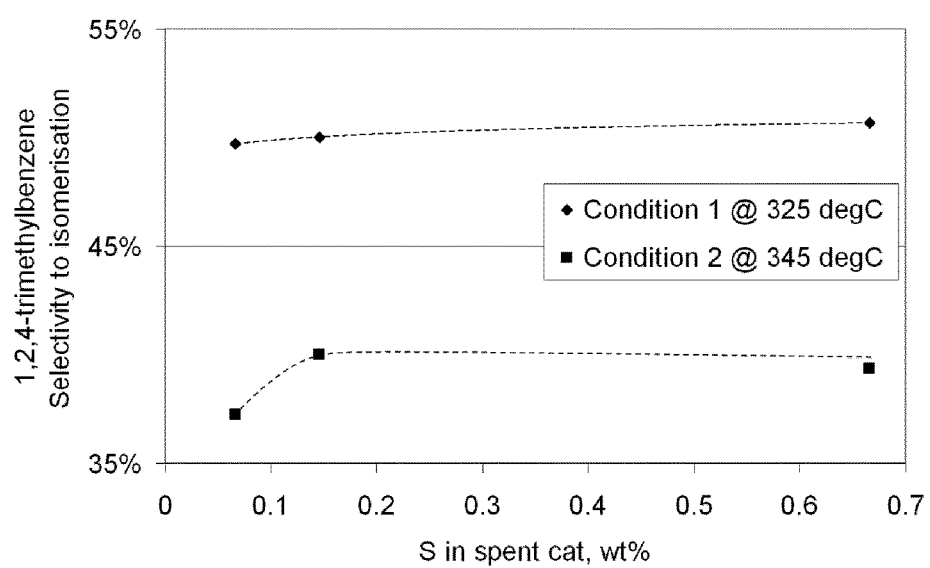
Figure 2. Conversion of 1,2,4-trimethylbenzene - Selectivity to isomerization

PROCESS AND CATALYST FOR UPGRADING GASOLINE

The present invention relates to a process for upgrading synthetic gasoline as obtained by catalytic conversion of e.g. methanol or methanol/dimethylether. More particularly, the invention provides a process wherein tetramethylbenzenes and trimethylbenzenes, in particular durene (1,2,4,5-tetramethylbenzene) and pseudocumene (1,2,4-trimethylbenzene), contained in the gasoline are isomerized or isomerized and dealkylated/disproportionated in the presence of hydrogen and in contact with a sulfided metal catalyst supported on a on an acidic carrier to provide gasoline with improved characteristics.

Durene (1,2,4,5-tetramethylbenzene) is one of the compounds formed during the conversion of e.g., methanol or methanol/dimethylether to gasoline. It has good octane numbers (estimated blend RON 154) but it has a very high freezing/melting point (79.2° C.). To avoid plugging problems in the vehicles engine filters in cold weather, durene content in the gasoline has to be limited to a low value, about 4-8 wt %, depending on regional climate.

Another characteristic of synthetic gasoline is the high concentration of pseudocumene (1,2,4-trimethylbenzene, blend RON/MON 148/124). Whilst it has good octane numbers, one of its isomers (mesitylene, 1,3,5-trimethylbenzene, blend RON/MON 171/137) has a much better octane rating and, therefore, it may be considered an octane booster.

Producing mesitylene (1,3,5-trimethylbenzene) simultaneously to reducing durene (1,2,4,5-tetramethylbenzene) can compensate for any loss in octane incurred by hydrogenation and dealkylation/disproportionation reactions of other aromatic and olefinic compounds in the gasoline and even improve the octane number in the final product.

We have found that when hydrotreating gasoline fractions containing tetra- and tri-methylbenzenes, including durene (1,2,4,5-tetramethylbenzene) and pseudocumene (1,2,4-trimethylbenzene), in presence of a sulfided metal catalyst supported on an acidic carrier it is possible to reduce content of durene and increase content of mesitylene (1,3,5-trimethylbenzene) in the gasoline fractions.

Thus, this invention provides a process for upgrading gasoline containing durene (1,2,4,5-tetramethylbenzene) and pseudocumene (1,2,4-trimethylbenzene). The process comprises hydroisomerization of durene and pseudocumene contained in the gasoline in the presence of a catalyst comprising a hydrogenation-dehydrogenation function, which is provided by a sulfided base metal, and an acid function, which is provided by supporting the sulfided base metal on an acidic carrier, thereby converting durene (1,2,4,5-tetramethylbenzene) to isodurene (1,2,3,5-tetramethylbenzene) and prehnitene (1,2,3,4-tetramethylbenzene) and converting pseudocumene (1,2,4-trimethylbenzene) to mesitylene (1,3,5-trimethylbenzene) and hemimellitene ((1,2,3-trimethylbenzene).

In addition to the hydrogenation-dehydrogenation activity existing on the metallic sites, there is also a certain degree of cracking or hydrogenolysis activity. In our invention, a high selectivity towards isomerization is obtained by reducing/controlling the hydrogenolysis function of the metal site by means of sulfidation.

The metal can be sulfided in-situ by processing a sulfur-containing feed, e.g., a synthetic gasoline with a sulfur dopant, e.g. dimethyldisulfide (DMDS), ditertbutyldisulfide (TBDS), etc or a sulfur-containing refinery straight-run naphtha, as only very small amounts of sulfur are necessary.

The catalyst can alternatively be sulfided by simply processing an $H_2S$-containing hydrogen-rich gas.

In an embodiment of the invention, the sulfided base metal in the catalyst is nickel. The metal content in the catalyst is in the range of 0.5 to 20 wt %, preferably in the range of 1 to 5 wt %.

In further an embodiment, the carrier comprises an acidic zeolite.

Preferably, the zeolite comprises ZSM-5 with a $SiO_2/Al_2O_3$ ratio in the range of 15 to 300, preferably in the range 20 to 30.

In still an embodiment, the carrier comprises a mixture of an acidic zeolite and alumina binder material. The weight content of zeolite is the range 15% to 99%, preferably in the range 20% to 80%, more preferably in the range 30% to 75% and still more preferably in the range 40% to 70% by weight.

Preferably, the catalyst is composed of 1-5 wt % nickel, 50-70 wt % ZSM-5, 50-30 wt % alumina binder.

In presence of a sulfided nickel catalyst supported on a carrier comprising a mixture of ZSM-5 zeolite and alumina, durene (1,2,4,5-tetramethylbenzene) is almost exclusively isomerized to isodurene (1,2,3,5-tetramethylbenzene) and prehnitene (1,2,3,4-tetramethylbenzene), which have much lower melting points and solves the freezing point problem.

Whilst durene (1,2,4,5-tetramethylbenzene) is neither substantially dealkylated nor hydrogenated, which is desirable to keep product yield, limit hydrogen consumption to a minimum and avoid loss of octane number, pseudocumene (1,2,4-trimethylbenzene) is advantageously isomerized to mesitylene (1,3,5-trimethylbenzene) and hemimellitene (1,2,3-trimethylbenzene).

Mesitylene has a very high octane number and improves the octane numbers in the final gasoline product.

In the upgrading process, the gasoline is combined with a hydrogen-rich gas, preheated to reaction temperature (temperature in the range of 250-400° C., preferably in the range of 290-370° C.) and then processed over the catalyst above disclosed operating in a pressure range of 0.1 to 5 MPa, preferably in the range of 1-3 MPa. The reactor effluent is cooled after reaction, e.g. by heat-exchanging with the reactor feed. The upgraded gasoline is separated from the gas, which is then pressurized in a compressor and recycled. The upgraded gasoline is low in durene (1,2,4,5-tetramethylbenzene) content, and consequently its cold flow properties (e.g., pour and cloud point) are adequate whilst the octane rating has been improved compared to that of the feed as a consequence of the formation of mesitylene (1,3,5-trimethylbenzene) and due to the absence of aromatics saturation.

As mentioned hereinbefore, trimethylbenzenes and tetramethylbenzenes are typically present in synthetic gasoline produced from catalytic conversion of e.g. methanol or methanol/dimethylether. The synthetic gasoline additionally contains olefinic compounds. If the olefinic components are sent to the hydroisomerization process, they would be hydrogenated fairly easily thus causing octane loss.

Thus, in a further embodiment of the invention, the gasoline is fractionated into a light fraction containing olefinic components and a heavy, predominantly aromatic, fraction prior to contact with the catalyst and the heavy fraction is subjected the upgrading process in accordance with the invention.

The upgraded heavy fraction is subsequently blended with the light fraction containing the olefinic material to produce a final full range gasoline product with conserved or even improved octane rating.

The invention further provides a catalyst for use in hydroisomerization of durene (1,2,4,5-tetramethylbenzene) and pseudocumene contained in gasoline comprising a sulfided base metal supported on an acidic carrier.

In an embodiment, the sulfided metal in the catalyst comprises nickel. The content of nickel is preferably 0.5 to 20 wt %.

In further an embodiment, the acidic carrier comprises a zeolite.

A suitable zeolite is ZSM-5. The ZSM-5 has preferably a SiO2/Al2O3 ratio in the range of 25 to 300.

In yet an embodiment, the acidic carrier further comprises alumina.

In a preferred embodiment, the catalyst consists of 1-5 wt % sulfided nickel, 50-70 wt % ZSM-5 and 50-30 wt % alumina binder.

EXAMPLE 1

The catalyst was prepared by impregnating cylindrical extrudates comprising ZSM-5 and alumina with aqueous Ni nitrate, followed by calcination in air. A 100 ml fixed bed of the catalyst was loaded in an isothermal fixed-bed reactor (1.5 cm approximate internal diameter) and sulfidation of the catalyst was carried out by hydrotreating a sulfur-containing naphtha fraction.

After sulfidation was completed, a model heavy gasoline with the composition shown in Table 1 was treated by mixing the model feed with pure hydrogen, heating to reaction temperature and carrying out the isomerization reactions in the presence of the sulfided catalyst. The reactor product was separated in a high pressure and low pressure separators. Total liquid product samples from the low pressure separator were taken and analyzed.

Table 2 shows the test conditions, measured hydrogen consumption and product yield whilst the composition, calculated RON (by Detailed Hydrocarbon Analysis), pour and cloud points are shown in Table 3.

TABLE 1

Model heavy gasoline

| | Compound | wt % |
|---|---|---|
| A9 | Pseudocumene (1,2,4-trimethylbenzene) | 46.2% |
| A10 | Durene (1,2,4,5-tetramethylbenzene) | 25.3% |
| A10 | diethylbenzene | 15.4% |
| N8 | 1,2-dimethylcyclohexane | 1.1% |
| A8 | xylenes | 8.8% |
| A11 | pentamethylbenzene | 1.0% |
| A10 | naphthalene | 2.2% |

TABLE 2

Conditions, H2 consumption, product yields.

| | | Time on stream | | | |
|---|---|---|---|---|---|
| Condition | h | 0 FEED | 211 Cond#1 | 453 cond#2 | 522 cond#3 |
| Pressure | barg | | 16 | 16 | 16 |
| Temperature | °C. | | 325 | 305 | 345 |
| LHSV | 1/h | | 0.98 | 0.50 | 0.50 |
| H2/liquid feed | Nl/l | | 156 | 305 | 303 |
| H2 consumption | Nl/l | | 8 | 5 | 18 |
| Yields | | | | | |
| C1-C4 | wt. % FF | 0.00 | 1.81 | 1.19 | 4.41 |
| C5-140° C. | wt. % FF | 7.60 | 15.40 | 12.55 | 21.17 |
| 140-150° C. | wt. % FF | 1.80 | 1.96 | 1.58 | 3.44 |
| 150-160° C. | wt. % FF | 0.00 | 0.88 | 0.49 | 1.24 |
| 160-170° C. | wt. % FF | 19.50 | 20.22 | 18.16 | 25.01 |
| 170° C.+ | wt. % FF | 71.1 | 59.77 | 66.04 | 44.87 |
| C5+ | wt. % FF | 100.00 | 98.24 | 98.83 | 95.73 |
| C4+ | wt. % FF | 100.00 | 98.69 | 99.20 | 96.58 |

FF = fresh feed

TABLE 3

Conditions, composition and selected properties.

| | | Time on stream | | | |
|---|---|---|---|---|---|
| Condition | h | 0 FEED | 211 cond#1 | 453 cond#2 | 522 cond#3 |
| Pressure, barg | barg | | 16 | 16 | 16 |
| Temperature | °C. | | 325 | 305 | 345 |
| LHSV | 1/h | | 0.98 | 0.50 | 0.50 |
| H2/liquid feed | Nl/1 | | 156 | 305 | 303 |
| Liquid Recovery | wt. % FF | 100.0 | 98.15 | 98.71 | 95.47 |
| COMPOSITION | | | | | |
| Durene(1,2,4,5-Tetramethylbenzene) | wt % TLP | 25.54 | 19.6 | 21.2 | 12.9 |
| Pseudocumene (1,2,4-Trimethylbenzene) | wt % TLP | 45.4 | 37.3 | 40.4 | 26.2 |
| Mesitylene (1,3,5-Trimethylbenzene) | wt % TLP | 0.1 | 2.5 | 1.9 | 5.6 |
| CONVERSION | | | | | |
| Durene(1,2,4,5-Tetramethylbenzene) | Wt % | 0% | 23% | 17% | 49% |
| Pseudocumene (1,2,4-Trimethylbenzene) | Wt % | 0% | 18% | 11% | 42% |
| SUBTOTALS | | | | | |
| Sum tetramethyl-benzenes | wt % TLP | 26 | 26 | 26 | 26 |
| Sum trimethyl-benzenes | wt % TLP | 46 | 41 | 43 | 34 |
| Sum xylenes + ethylbenzenes | wt % TLP | 8 | 15 | 13 | 18 |
| Sum diethylbenzenes | wt % TLP | 15 | 7 | 9 | 4 |
| Toluene | wt % TLP | 0 | 1 | 1 | 4 |
| Benzene | wt % TLP | 0 | 1 | 0 | 3 |
| Ratio of mesitylene (1,3,5-Trimethyl-benzene) to sum of trimethyl-benzenes | | 0.3% | 6% | 4% | 16% |
| Calculated RON | | | 94 | 97 | 96 | 100 |
| Pour Point | °C. | 14 | −1 | 5 | −23 |
| Cloud Point | °C. | 16 | 2 | 8 | −22 |

FF = fresh feed
TLP = total liquid product

Pour point can be improved by 20 degrees at 30 wt % durene (1,2,4,5-tetramethylbenzene) conversion and by 37 degrees at 50 wt % conversion. At 30 and 50 wt % durene conversion, the respective gain in (calculated) RON is 4 and 6. Hydrogen consumption is less than 18 Nl/l (0.11 mol/mol)

EXAMPLE 2

The catalyst was prepared by impregnating cylindrical extrudates comprising ZSM-5 and alumina with aqueous Ni nitrate, followed by calcination in air. 3.8 g of the catalyst was loaded in the reactor.

A full range synthetic gasoline produced by converting methanol over H-ZSM-5 at 340-400° C. and a pressure of 1.5 MPa was fractionated into a light and heavy gasoline with a sulfur content of less than 10 wppm. Properties of the heavy gasoline are shown in Table 4. A portion of the heavy gasoline fraction was then doped with dimethyldisulfide (DMDS) to give a final sulfur content of 138 wt ppm.

TABLE 4

Properties of the heavy gasolines

|  | Heavy gasoline |
|---|---|
| Sulfur, wt % | <0.0010 |
| Hydrogen, wt % | 10.61 |
| Specific Gravity 60/60° F. | 0.8672 |
| Cloud Point, ° C. | 1.4 |
| Pour Point, ° C. | −2 |
| Durene (1,2,4,5-tetramethylbenzene) content, wt % | 19.7 |
| Calculated RON | 87.3 |
| Boiling point distribution | |
| 0.5 wt % (IBP), ° C. | 97 |
| 5 wt %, ° C. | 137 |
| 10 wt %, ° C. | 139 |
| 15 wt %, ° C. | 144 |
| 20 wt %, ° C. | 160 |
| 30 wt %, ° C. | 168 |
| 40 wt %, ° C. | 170 |
| 50 wt %, ° C. | 171 |
| 60 wt %, ° C. | 180 |
| 70 wt %, ° C. | 196 |
| 80 wt %, ° C. | 198 |
| 85 wt %, ° C. | 198 |
| 90 wt %, ° C. | 199 |
| 95 wt %. ° C. | 221 |
| 99.5 wt % (FBP), ° C. | 299 |

In test A, the sulfidation was carried out by heating the reactor up to 150° C. @ 5° C./min (H2 flow=250 Nml/min, P=50 barg). Then feeding the 138 wt ppm S-doped heavy gasoline at a rate of 0.1 ml/min (equivalent to WHSV=1.36 h-1). H2 flow is then set to 30 Nml/min (H2/oil=300 Nml/ml), and subsequently heating up again to 325° C. @ 2° C./min. After 4 hours at 350° C., the sulfidation mixture is switched to the <10 wt ppm heavy gasoline.

In test B, the catalyst was sulfided with a mixture of 2.5 wt % DMDS in n-C7. All of the DMDS is thermally decomposed in the preheater to H2S. The sulfidation was carried out by heating the reactor up to 150° C. @ 5° C./min (H2 flow=250 Nml/min, P=50 barg). Then feeding the sulfidation mixture at a rate of 0.3 ml/min (equivalent to LHSV=3.3 h-1 and H2/oil=833 Nml/ml), and subsequently heating up again to 350° C. @ 2° C./min. After 4 hours at 350° C., the sulfidation mixture is switched to the 138 wt ppm S-doped heavy gasoline.

In test C, the reactor is heated up to 150° C. @ 5° C./min (H2 flow=250 Nml/min, P=50 barg). Then feeding the less than 10 wt ppm S heavy gasoline at a rate of 0.1 ml/min (equivalent to WHSV=1.36 h-1). H2 flow is then set to 30 Nml/min (H2/oil=300 Nml/ml), and subsequently heating up again to 325° C. @ 2° C./min.

In tests A-C, the heavy gasoline was treated by mixing it with pure hydrogen, at a WHSV=1.4 h-1 and H2/oil=300 Nl/l (approx 1.9 mol/mol) and testing at two different conditions. In cond#1 temperature was set at T=324° C., whilst cond#2 was at T=344° C. and each condition ran for about 25 hours.

The reactor product was separated in a system comprising a high pressure and low pressure separators. The composition of the liquid phase in the high pressure separator was analysed by gas chromatography.

After each test, the spent catalyst was characterized and the measured sulfur content of the spent catalyst of tests A-C is used as an indicative parameter of the degree of sulfidation of the metal in the catalyst.

FIG. 1 in the drawings shows that, as the upgrading takes place in the presence of hydrogen, it is necessary to add sulfur to the metallic nickel in order to reduce the rapid hydrogenolysis/cracking that forms light hydrocarbons.

FIG. 2 in the drawings shows that in the transformation of 1,2,4-trimethylbenzene (pseudocumene), the selectivity to isomerization products, i.e., 1,3,5-trimethylbenzene (mesitylene) and 1,2,3-trimethylbenzene (hemimellitene), increases by having added small quantities of sulfur, particularly at 345° C.

The invention claimed is:

1. A process for upgrading a synthetic gasoline comprising durene (1, 2, 4, 5-tetramethylbenzene) and pseudocumene (1, 2, 4-trimethylbenzene) derived from catalytic conversion of methanol or a methanol-dimethylether mixture, the process comprising hydroisomerization of durene and pseudocumene contained in the synthetic gasoline in presence of hydrogen, a catalyst comprising sulfided nickel supported on an acidic carrier, and a sulfur dopant to produce an upgraded synthetic gasoline, wherein durene (1, 2, 4, 5-tetramethylbenzene) is converted to isodurene (1, 2, 3, 5-tetramethylbenzene) and prehnitene (1, 2, 3, 4-tetramethylbenzene) and pseudocumene (1, 2, 4-trimethylbenzene) is converted to mesitylene (1, 3, 5-trimethylbenzene), said upgraded synthetic gasoline has a reduced durene and pseudocumene content and an increased combined isodurene and prehnitene content relative to said synthetic gasoline, and the upgraded synthetic gasoline has at least the same octane rating as the synthetic gasoline.

2. The process of claim 1, wherein the catalyst has a nickel content of 0.5 to 20 wt %.

3. The process of claim 1, wherein the acidic carrier comprises a zeolite.

4. The process of claim 3, wherein the zeolite has a $SiO_2/Al_2O_3$ ratio in the range of 15 to 300.

5. The process of claim 3, wherein the zeolite comprises ZSM-5.

6. The process of claim 1, wherein the acidic carrier comprises alumina.

7. The process of claim 1, wherein the catalyst is supported on a mixture of ZSM-5 and alumina.

8. The process of claim 7, wherein the catalyst comprises 1-5 wt % nickel, and an acidic carrier comprising the ZSM-5 and alumina in a ratio between 50:50 and 70:30.

9. The process of claim 1, further comprising a step of separating a light fraction from the synthetic gasoline and by-passing the light fraction around the hydroisomerization.

10. The process according to claim 1, wherein hydroisomerization conditions include a temperature of between 250° and 400° C.

11. The process of claim 1, wherein the synthetic gasoline includes more pseudocumene than durene.

* * * * *